(12) United States Patent
Hasenberg et al.

(10) Patent No.: US 10,544,094 B2
(45) Date of Patent: Jan. 28, 2020

(54) BETA-MERCAPTOETHANOL SYNTHESIS

(71) Applicant: Chevron Phillips Chemical Company LP, The Woodlands, TX (US)

(72) Inventors: Daniel M. Hasenberg, Kingwood, TX (US); Alex Pauwels, Deurne (BE)

(73) Assignee: Chevron Philips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 15/632,994

(22) Filed: Jun. 26, 2017

(65) Prior Publication Data

US 2017/0291873 A1 Oct. 12, 2017

Related U.S. Application Data

(62) Division of application No. 14/959,328, filed on Dec. 4, 2015, now Pat. No. 9,718,767.

(51) Int. Cl.
*B01J 8/02* (2006.01)
*C07C 319/04* (2006.01)
(Continued)

(52) U.S. Cl.
CPC ............. *C07C 319/04* (2013.01); *B01J 8/001* (2013.01); *B01J 8/02* (2013.01); *B01J 8/0292* (2013.01);
(Continued)

(58) Field of Classification Search
CPC ... C07C 319/04; C07C 319/02; C07C 319/08; C07C 323/12; B01J 8/001; B01J 8/02; B01J 8/0292
(Continued)

(56) References Cited

U.S. PATENT DOCUMENTS 2,776,997 A 1/1957 Doumani
3,086,997 A 4/1963 Warner
(Continued)

FOREIGN PATENT DOCUMENTS

CN 101941928 A 1/2011
DE 2129162 A1 12/1971
(Continued)

OTHER PUBLICATIONS

McNaught, Alan D., et al., "Compendium of Chemical Terminology," IUPAC Recommendations, Second edition, 1997, 5 pages, Wiley-Blackwell.
(Continued)

*Primary Examiner* — Huy Tram Nguyen
(74) *Attorney, Agent, or Firm* — Conley Rose, P.C.

(57) ABSTRACT

A process includes reacting, in a reactor having a fixed bed containing a solid catalyst which contains a heterogeneous ion exchange resin, hydrogen sulfide and ethylene oxide in the presence of the solid catalyst to yield a reaction product which contains beta-mercaptoethanol. A reactor system includes the reactor, an ethylene oxide stream, a hydrogen sulfide stream, a fixed bed containing the solid catalyst placed in the reactor, and an effluent stream containing the reaction product. During steady state operation of the reactor in the process and the reactor system, the hydrogen sulfide and the ethylene oxide are present in a mole ratio in a range of about 9:1 to about 20:1.

14 Claims, 1 Drawing Sheet

(51) Int. Cl.
*C07C 319/02* (2006.01)
*B01J 8/00* (2006.01)
*C07C 319/08* (2006.01)
*C07C 323/12* (2006.01)
*C07D 303/02* (2006.01)

(52) U.S. Cl.
CPC .......... *C07C 319/02* (2013.01); *C07C 319/08* (2013.01); *C07C 323/12* (2013.01); *B01J 2208/00513* (2013.01); *B01J 2208/00548* (2013.01); *B01J 2208/024* (2013.01); *B01J 2208/025* (2013.01); *C07D 303/02* (2013.01)

(58) Field of Classification Search
USPC ........................................................ 422/129
See application file for complete search history.

(56) References Cited

U.S. PATENT DOCUMENTS

| | | | |
|---|---|---|---|
| 3,290,383 | A | 12/1966 | Pflugfelder et al. |
| 3,366,693 | A | 1/1968 | Randall et al. |
| 3,394,192 | A | 7/1968 | Jones |
| 3,462,496 | A | 8/1969 | Fletcher et al. |
| 3,574,768 | A | 4/1971 | Tompkins |
| 3,662,004 | A | 5/1972 | Umbach et al. |
| 3,710,439 | A | 1/1973 | Goetze et al. |
| 4,083,876 | A | 4/1978 | Bruns et al. |
| 4,281,202 | A | 7/1981 | Buchholz et al. |
| 4,398,042 | A | 8/1983 | Kleemann et al. |
| 4,493,938 | A * | 1/1985 | Shimamoto ........... C07C 323/00 568/62 |
| 4,507,505 | A | 3/1985 | Arretz |
| 4,564,710 | A | 1/1986 | Steger |
| 4,985,586 | A | 1/1991 | Arretz et al. |
| 9,718,767 | B2 | 8/2017 | Hasenberg et al. |
| 2007/0135658 | A1* | 6/2007 | Hasenberg ............ C07C 319/08 568/38 |
| 2008/0242894 | A1* | 10/2008 | Hasenberg ............. B01J 23/882 568/61 |

FOREIGN PATENT DOCUMENTS

| | | |
|---|---|---|
| EP | 0039062 A1 | 11/1981 |
| EP | 1923384 A1 | 5/2008 |
| GB | 585655 | 2/1947 |
| GB | 988135 | 4/1965 |
| GB | 1296452 | 11/1972 |
| GB | 2077263 A | 12/1981 |
| JP | 60058932 A | 4/1985 |
| JP | 2006184251 A | 7/2006 |
| JP | 2008013453 A | 1/2008 |
| RU | 2556859 C1 | 7/2015 |

OTHER PUBLICATIONS

Foreign communication from the related application International Application No. PCT/US2016/064133, International Search Report and Written Opinion, dated Feb. 17, 2017, 13 pages.

Andruski, R., et al., "Studies on the synthesis of 2-mercaptoethanol" Organika, Instytut Przemyslu Organicznego, Poland, Jan. 1, 1979, pp. 15-23, XP009182190.

* cited by examiner

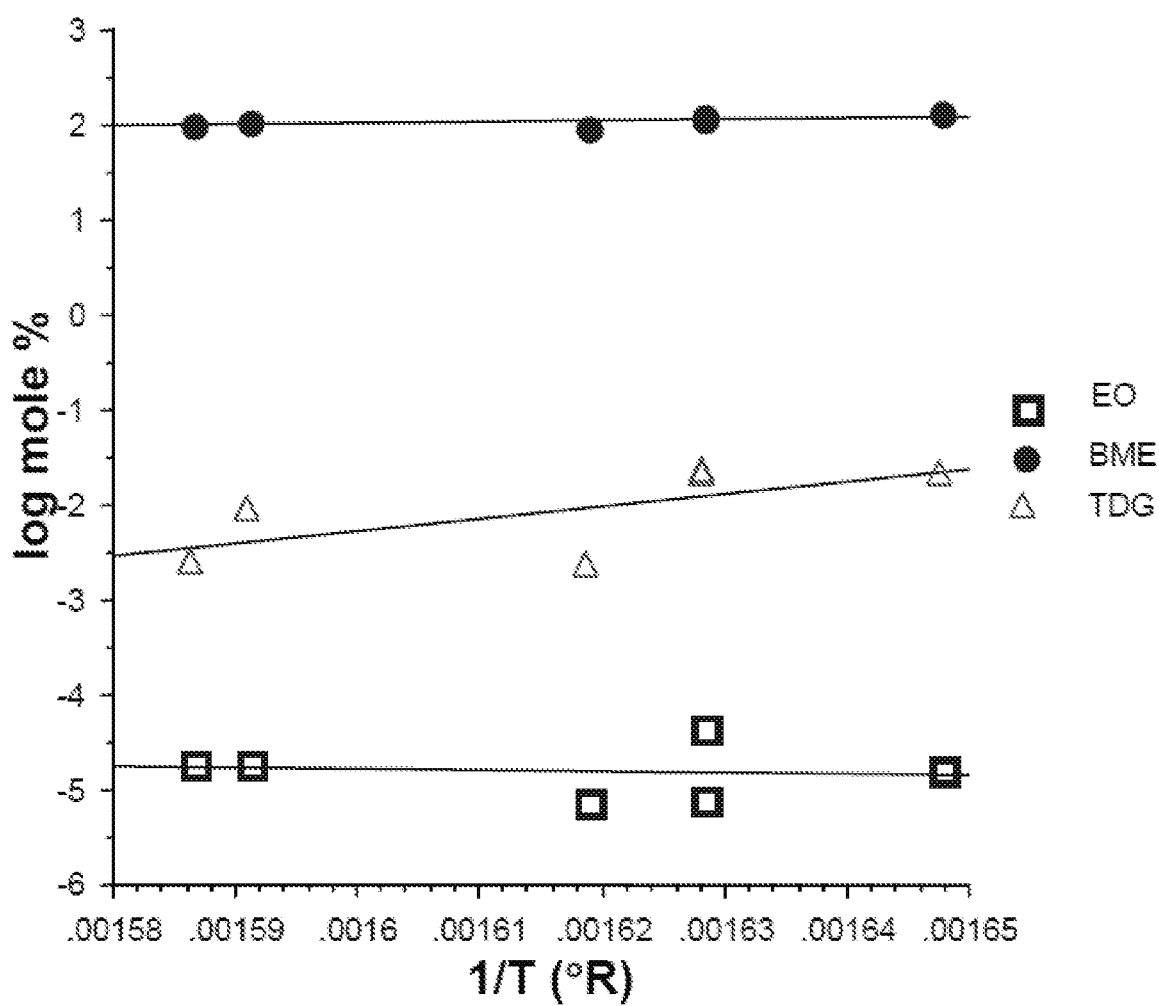

ized by a LEWATIT® MP 62 resin-catalyzed beta-mercaptoethanol synthesis from ethylene oxide and hydrogen sulfide.

BETA-MERCAPTOETHANOL SYNTHESIS

CROSS-REFERENCE TO RELATED APPLICATIONS

This application is a divisional of and claims priority to U.S. patent application Ser. No. 14/959,328 filed Dec. 4, 2015, published as U.S. Patent Application Publication No. US 2017/0158630 A1 and entitled "Beta-Mercaptoethanol Synthesis," which is incorporated by reference herein in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD

This disclosure relates to the synthesis of beta-mercaptoethanol via the conversion of ethylene oxide.

BACKGROUND

Beta-mercaptoethanol (BME) is mainly used in poly(vinyl chloride) (PVC) production as an intermediate for the synthesis of PVC heat stabilizers and as a process regulator in PVC manufacturing. BME is a common reducing agent and is also used as a component in corrosion inhibitors, as a processing aid for the leather industry, and as a laboratory chemical in biochemical applications. BME is generally produced via reaction of ethylene oxide (EO) with hydrogen sulfide ($H_2S$) in a continuous stirred-tank reactor (CSTR) in the presence of excess hydrogen sulfide ($H_2S$). However, in a CSTR, conversion of ethylene oxide to BME is limited, and undesirable byproducts such as thiodiglycol and other heavy products are also produced. Thus, there is an ongoing need for developing methods for producing BME.

SUMMARY

Disclosed is a process comprising reacting, in a reactor having a fixed bed containing a solid catalyst comprising a heterogeneous ion exchange resin, hydrogen sulfide and ethylene oxide in the presence of the solid catalyst to yield a reaction product comprising beta-mercaptoethanol, wherein during steady state operation of the reactor, the hydrogen sulfide and the ethylene oxide are present in a mole ratio in a range of about 9:1 to about 20:1.

Also disclosed is a reactor system which includes a reactor; an ethylene oxide stream feeding ethylene oxide to the reactor; a hydrogen sulfide stream feeding hydrogen sulfide to the reactor; a fixed bed containing a solid catalyst placed in the reactor; and an effluent stream flowing from the reactor, wherein the effluent stream comprises a reaction product comprising beta-mercaptoethanol yielded in the reactor by a reaction of hydrogen sulfide and ethylene oxide in presence of the solid catalyst; wherein the solid catalyst comprises a heterogeneous ion exchange resin, and wherein the hydrogen sulfide and the ethylene oxide are present in the reactor during steady state operation in a mole ratio ranging from about 9:1 to about 20:1.

BRIEF DESCRIPTION OF THE DRAWINGS

For a detailed description of the preferred embodiments of the disclosed processes, reference will now be made to the accompanying drawing in which:

FIG. 1 displays an Arrhenius plot of activation energies for a LEWATIT® MP 62 resin-catalyzed beta-mercaptoethanol synthesis from ethylene oxide and hydrogen sulfide.

DETAILED DESCRIPTION OF THE EMBODIMENTS

Disclosed herein are embodiments of processes to produce beta-mercaptoethanol (BME) via conversion of ethylene oxide (EO) to beta-mercaptoethanol in an excess of hydrogen sulfide ($H_2S$) and in the presence of a solid catalyst. In an embodiment, the ethylene oxide can react with hydrogen sulfide in a reactor comprising a fixed bed containing a solid catalyst comprising a heterogeneous ion exchange resin. In some embodiments, the solid catalyst can have weakly basic active groups to allow for conversion of ethylene oxide by hydrogen sulfide.

The following definitions are provided in order to aid those skilled in the art in understanding the detailed description of the present invention. Unless otherwise defined herein, scientific and technical terms used in connection with the present invention shall have the meanings that are commonly understood by those of ordinary skill in the art to which this invention belongs. Further, unless otherwise required by context, singular terms shall include pluralities and plural terms shall include the singular.

Unless explicitly stated otherwise in defined circumstances, all percentages, parts, ratios, and like amounts used herein are defined by weight.

Further, certain features of the present invention which are, for clarity, described herein in the context of separate embodiments, may also be provided in combination in a single embodiment. Conversely, various features of the invention that are, for brevity, described in the context of a single embodiment, may also be provided separately or in any sub-combination.

If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

As used herein, beta-mercaptoethanol (BME) can also be referred to by various synonyms including, but not limited to, 2-sulfanylethanol (IUPAC name), 2-hydroxy-1-ethanethiol, thioglycol, 2-mercaptoethanol, 2-thioethanol, 2-hydroxyethyl mercaptan, and others. As used herein, ethanedithiol can also be referred to by various synonyms, including, but not limited to, ethane-1,2-dithiol (IUPAC name), 1,2-ethanedithiol, 1,2-dimercaptoethane, dithioglycol, ethylene mercaptan, and others. As used herein, thiodiglycol can also be referred to by various synonyms including, but not limited to, 2-(2-hydroxyethylsulfanyl) ethanol (IUPAC name), 2,2'-thiodiethanol, thiodiethanol, thiodiethylene glycol, and others.

Regarding claim transitional terms or phrases, the transitional term "comprising," which is synonymous with "including," "containing," "having," or "characterized by,"

is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claim. A "consisting essentially of" claim occupies a middle ground between closed claims that are written in a "consisting of" format and fully open claims that are drafted in a "comprising" format. Absent an indication to the contrary, describing a compound or composition as "consisting essentially of" is not to be construed as "comprising," but is intended to describe the recited component that includes materials which do not significantly alter the composition or method to which the term is applied. For example, a feedstock consisting essentially of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class to which it is utilized, and it is possible to have different transitional terms or phrases utilized with different features within a claim. For example, a method can comprise several recited steps (and other non-recited steps), but utilize a catalyst system consisting of specific components; alternatively, consisting essentially of specific components; or alternatively, comprising the specific components and other non-recited components.

In this disclosure, while systems, processes, and methods are often described in terms of "comprising" various components, devices, or steps, the systems, processes, and methods can also "consist essentially of" or "consist of" the various components, devices, or steps, unless stated otherwise.

The term "about" as used herein means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

Although any methods, devices, and materials similar or equivalent to those described herein can be used in the practice or testing of the invention, the typical methods, devices, and materials are herein described.

In an embodiment, a process for producing beta-mercaptoethanol (BME) can comprise reacting, in a reactor having a fixed bed containing a solid catalyst comprising a heterogeneous ion exchange resin, hydrogen sulfide and ethylene oxide in the presence of the solid catalyst to yield a reaction product comprising BME.

In an embodiment, the reactor can comprise any suitable fixed bed catalytic reactor. Generally, a fixed bed catalytic reactor contains a fixed bed of solid catalyst, wherein the solid catalyst does not move with respect to a fixed or immobile reference point on a reactor body. The solid catalyst can be retained in the fixed bed by any suitable methodology, such as for example by employing retaining screens.

In an embodiment, the fixed bed catalytic reactor can be a continuous flow reactor, such as a plug flow reactor (PFR). Generally, a PFR, also known as a flow tube reactor, comprises a fluid flowing through the reactor as a series of infinitely thin coherent "plugs," each plug having a uniform composition, traveling in the axial direction of the flow tube reactor. In PFRs, it is assumed that as a plug flows through the reactor, the fluid is perfectly mixed in the radial direction, but not in the axial direction (forwards or backwards).

In an embodiment, the reactor can be an adiabatic reactor. Generally, adiabatic reactors do not provide for heat exchange between the interior of the reactor (e.g., catalyst, catalyst bed, reactants, etc.) and the surroundings of the reactor. In an embodiment, no internal and/or external cooling source is used to cool the reactor. For purposes of the disclosure herein, the term "internal cooling" excludes evaporative cooling due to (e.g., owing to) hydrogen sulfide converting from a liquid phase to a vapor phase, thereby absorbing a heat of reaction. In embodiments, cooling equipment which are not used for external cooling include heat exchangers and reactor jackets. In embodiments, cooling equipment which are not used for internal cooling include internal heat exchange elements (e.g., heat exchange elements that would be placed inside the reactor) that can contain a heat transfer medium (i.e., a heat transfer fluid such as water, mineral oil(s), synthetic or organic based fluid(s), or combinations thereof). Further, for purposes of the disclosure herein, the terms "internal cooling" and "external cooling" refer to cooling by heat exchange based on energy input outside of the reactor. The adiabatic reactor as used herein can be a "self-cooling" reactor via converting (e.g., evaporating) hydrogen sulfide from a liquid phase to a vapor phase. As will be appreciated by one of skill in the art, and with the help of this disclosure, the reaction of ethylene oxide with hydrogen sulfide to produce BME is exothermic, as will be discussed in more detail later herein.

In an embodiment, the solid catalyst can comprise any suitable basic solid catalyst. In an embodiment, the solid catalyst comprises a heterogeneous ion exchange resin. Generally, heterogeneous catalysts refer to catalysts that are in a different phase than the reactants for which they catalyze a reaction. For example, the heterogeneous ion exchange resin can be a solid, while ethylene oxide and hydrogen sulfide can be in a liquid (or gas) phase contacting the solid resin catalyst. Generally, ion exchange resins are polymers containing loosely held ions, and the polymers are capable of exchanging such ions with other ions in solutions that come in contact with the polymer. These ion exchanges can take place without any physical alteration to the ion exchange material. Ion exchange resins are insoluble acids or bases that have salts which are also insoluble, and this enables exchange of either positively charged ions (e.g., basic ion exchange resins or cation exchangers) or negatively charged ions (e.g., acidic ion exchange resins or anion exchangers).

Ion exchange resins generally consist of a crosslinked polymer matrix with a relatively uniform distribution of active ion exchange sites throughout the structure. In an embodiment, the polymer matrix suitable for use in the present disclosure as part of the ion exchange resin comprises polystyrene, copolymers of styrene and divinylbenzene (DVB), polyacrylic esters, polyethyleneimine, polyethylene, polypropylene, copolymers thereof, and the like, or combinations thereof.

In some embodiments, the solid catalyst can have basic active groups. In other embodiments, the solid catalyst can have weakly basic active groups. For purposes of the disclosure herein, the term "active group" or "active groups" when used to describe the catalyst refers to groups active for ion exchange. In an embodiment, the basic active groups can comprise quaternary ammonium groups. In an embodiment, the weakly basic active groups can comprise primary amine groups, secondary amine groups, tertiary amine groups, and the like, or combinations thereof. As will be appreciated by one of skill in the art, and with the help of this disclosure, primary, secondary and tertiary amine groups show weak basicity, and as such can be referred to as weakly basic active groups.

Nonlimiting examples of weakly basic active groups suitable for use in the current disclosure as part of the solid catalyst include alkyl amines, monoalkyl amine, dialkyl amine, dimethyl amine, trialkyl amines, and the like, or combinations thereof.

In an embodiment, the solid catalyst can comprise a styrene-DVB copolymer with weakly basic active groups comprising alkyl amines.

Commercial examples of solid catalysts suitable for use in the current disclosure include AMBERLYST® A21 resin which is an industrial grade weakly basic polymeric resin in bead form commercially available; and LEWATIT® MP 62 resin which is weakly basic, and macroporous anion exchange resin with tertiary amine groups (monofunctional) commercially available.

In an embodiment, the fixed bed of the solid catalyst can further comprise a chemically inert solid diluent or bulking material. Nonlimiting examples of chemically inert solid diluents suitable for use in the current disclosure as part of the fixed bed include fused alumina, polystyrene, copolymers of styrene and divinylbenzene (DVB), polyacrylic esters, polyethylene, polypropylene, copolymers thereof, and the like, or combinations thereof.

In some embodiments, the fixed bed of the solid catalyst can comprise a single zone (e.g., single catalytic zone) comprising the solid catalyst and optionally the chemically inert solid diluent, for example the bed materials being uniformly mixed.

In other embodiments, the fixed bed of the solid catalyst can comprise two or more zones (e.g., catalytic zones), wherein each zone comprises the solid catalyst and optionally the chemically inert solid diluent. When the fixed bed of the solid catalyst comprises two or more zones (e.g., catalytic zones), the solid catalyst can be distributed along the fixed bed according to a volumetric concentration gradient. For example, a volumetric concentration of the solid catalyst can increase from an entry point into a catalyst bed (e.g., reagents entry point(s)) to an exit point from the catalyst bed (e.g., reaction product exit point), e.g., a volumetric concentration of the solid catalyst can increase along a catalyst bed in the direction of the flow through a flow reactor. In some embodiments, an increase in the volumetric concentration of the solid catalyst can be continuous along a length of the fixed bed or zone thereof. In other embodiments, the increase in the volumetric concentration of the solid catalyst can be step-wise across a length of the fixed bed or zone thereof. As another example, a volumetric concentration of the solid catalyst can decrease from an entry point into a catalyst bed (e.g., reagents entry point(s)) to an exit point from the catalyst bed (e.g., reaction product exit point), e.g., a volumetric concentration of the solid catalyst can decrease along a catalyst bed in the direction of the flow through a flow reactor. As yet another example, a volumetric concentration of the solid catalyst can decrease along some regions or zones of the catalyst bed, increase along other regions of the catalyst bed, and stay the same along yet other regions of the catalyst bed. The amount of chemically inert solid diluent can likewise be adjusted or varied across the reactor bed geometry (e.g., along a length of the fixed bed or zone thereof) to provide a desired solid catalyst volumetric concentration profile.

In some embodiments, the solid catalyst can be distributed evenly along the fixed bed, e.g., the volumetric concentration of the catalyst can stay the same along a length of the fixed bed or zone thereof, for example uniformly mixed with chemically inert solid diluent, if present.

In an embodiment, the fixed bed of the solid catalyst can comprise a top zone, a middle zone, and a bottom zone, wherein the flow in the reactor can be from a top zone towards a bottom zone, and wherein the middle zone can be located between the top zone and the bottom zone. In such embodiment, the top zone comprises both a solid catalyst and a chemically inert solid diluent, wherein an amount of the chemically inert solid diluent by volume is greater (e.g., greater than 50%, 55%, 60%, 65%, 70%, 75%, 80%, 85%, 90%, 95%, or 99%, based on a total volume of the top zone) than an amount of the solid catalyst by volume in the top zone; the middle zone comprises both a solid catalyst and a chemically inert solid diluent, wherein an amount of the chemically inert solid diluent by volume is about the same (e.g., about 45/55, about 50/50, about 55/45, based on volumetric ratios of chemically inert solid diluent to solid catalyst in the middle zone) as an amount of the solid catalyst by volume in the middle zone; and wherein the bottom zone comprises a solid catalyst and a lesser amount by volume (e.g., less than 50%, 45%, 40%, 35%, 30%, 25%, 20%, 15%, 10%, 5%, 1%, or 0%, based on a total volume of the bottom zone) of the chemically inert solid diluent.

In an embodiment, the catalyst can be present in the fixed bed or any zone thereof in an amount of from about 10 vol. % to about 100 vol. %, alternatively from about 25 vol. % to about 100 vol. %, or alternatively from about 33 vol. % to about 66 vol. %, based on the total volume of the fixed bed or zone thereof.

In an embodiment, the fixed bed of the solid catalyst can comprise a top zone, a middle zone, and a bottom zone; wherein the top zone includes about 66% of a chemically inert solid diluent and about 33% solid catalyst by volume; wherein the middle zone includes about 50% of the chemically inert solid diluent and about 50% solid catalyst by volume; and wherein the bottom zone includes about 100% solid catalyst by volume.

In an embodiment, an ethylene oxide stream can feed ethylene oxide to the reactor. In an embodiment, a hydrogen sulfide stream can feed hydrogen sulfide to the reactor. In an embodiment, during steady state operation of the reactor, the hydrogen sulfide and the ethylene oxide can be present in a mole ratio of hydrogen sulfide to ethylene oxide in a range of from about 9:1 to about 20:1, alternatively from about 10:1 to about 19:1, or alternatively from about 11:1 to about 18:1. As will be appreciated by one of skill in the art, and with the help of this disclosure, hydrogen sulfide is always present in excess of the ethylene oxide. Prior to reaching a steady state operation of the reactor, hydrogen sulfide can be introduced to the reactor prior to introducing ethylene oxide to the reactor, such that there is always hydrogen sulfide present in excess of the ethylene oxide. Similarly, when the production needs to be stopped (e.g., reactor maintenance, catalyst regeneration, reactor troubleshooting, etc.), the ethylene oxide introduction to the reactor can be stopped first, followed by stopping the hydrogen sulfide introduction to the reactor. In some embodiments, a flow of hydrogen sulfide into the reactor could be maintained for a time period of from about 1 minute to about 1 hour, alternatively from about 5 minutes to about 45 minutes, or alternatively from about 15 minutes to about 30 minutes, prior to starting and/or subsequent to stopping the flow of ethylene oxide into the reactor. As will be appreciated by one of skill in the art, and with the help of this disclosure, the reactor is not at steady state while only hydrogen sulfide flows through the reactor, and there is no flow of ethylene oxide to the reactor, as both reactants are necessary to establish a steady state in the reactor. Further, as will be appreciated by one of skill in the art, and with the help of this disclosure, ethylene oxide is an extremely reactive compound, and as such it needs to be introduced to the reactor only when hydrogen sulfide is already present in the reactor, in order to avoid participation of ethylene oxide in any other reactions besides with hydrogen sulfide.

In an embodiment, the ethylene oxide stream and the hydrogen sulfide stream can each connect directly to the reactor without mixing ethylene oxide and hydrogen sulfide prior to introduction to the reactor. In such embodiment, the ethylene oxide stream and the hydrogen sulfide stream are separate streams introduced independent from each other to the reactor. In an embodiment, the ethylene oxide stream and the hydrogen sulfide stream can each be controlled independently from each other.

In an embodiment, a thermocouple can be placed in the ethylene oxide stream where it enters the reactor, wherein the thermocouple can be linked to a controller configured to stop a flow of the ethylene oxide stream upon detecting a temperature in the ethylene oxide stream which is above a threshold temperature. In some embodiments, the threshold temperature can be equal to or greater than about 30° C., alternatively equal to or greater than about 35° C., or alternatively equal to or greater than about 40° C. The threshold temperature is indicative of a reaction occurring. Since the reactor is adiabatic, temperature control in the reactor can occur by monitoring the amount of material available to react. As will be appreciated by one of skill in the art, and with the help of this disclosure, the reaction between ethylene oxide and hydrogen sulfide to produce BME is exothermic. Without wishing to be limited by theory, the reaction between ethylene oxide and hydrogen sulfide to produce BME is self-sustained (e.g., the reaction can progress by itself in the absence of an initiator and/or catalyst) at temperatures above 30-35° C., so if such temperatures are detected prior to reaching the catalyst bed, it indicates the reaction is occurring (for example, in an undesirable location outside the catalyst bed, or for example in a feed line to the reactor, a reactor head space, etc.).

In some embodiments, the reaction between ethylene oxide and hydrogen sulfide to produce BME can be restricted to the fixed bed comprising the heterogeneous ion exchange resin. Without wishing to be limited by theory, the heterogeneous ion exchange resin enables the formation of BME with only a very small amount of thiodiglycol (TDG) produced, and without any detectable formation of heavies such as ethanedithiol (EDT). However, if the ethylene oxide and hydrogen sulfide were to react in the absence of the heterogeneous ion exchange resin catalyst, such as upstream of the fixed bed, undesirable heavies such as EDT can form. As such, if a temperature above 30-35° C. indicative of reaction is detected in the reactor upstream of the fixed bed (and proximate to one or more thermocouples monitoring said temperature), then the flow of ethylene oxide can be stopped in order to stop the reaction outside the fixed bed, where reaction in the absence of the heterogeneous ion exchange resin catalyst could lead to formation of undesirable heavies such as EDT.

In some embodiments, the ethylene oxide stream and the hydrogen sulfide stream can each be connected to a mixing stream or a header such that ethylene oxide and hydrogen sulfide are mixed prior to introduction to the reactor. In such embodiments, a thermocouple can be placed in an end of the mixing stream or within the header which is connected to the reactor, wherein the thermocouple can be linked to a controller configured to stop a flow of the ethylene oxide stream upon detecting a temperature in the mixing stream which is above the threshold temperature, where threshold temperature is indicative of reaction (e.g., a reaction producing undesired EDT), as previously described herein.

In an embodiment, the hydrogen sulfide can be fed to the reactor in a downflow orientation. As the hydrogen sulfide travels along the length of the fixed bed of the reactor, a temperature of the fixed bed can increase along the length of the reactor in the direction of the flow, and some of the hydrogen sulfide will convert from a liquid phase to a gas phase (e.g., a portion of the liquid hydrogen sulfide will vaporize), thereby absorbing a portion of the reaction heat and controlling the temperature inside the reactor. The reactor is designed as an adiabatic packed bed reactor with no internals for transferring the heat of reaction. The diameter is sufficiently large so that the heat transferred through the outside walls is small relative to the heat released by the reaction. The EO and $H_2S$ feeds enter the top of the reactor as a liquid. Once entering the catalyst bed the heat of reaction converts at least a portion of the liquid $H_2S$ into a gas. Then the reactor is operated as a typical trickle-bed reactor with liquid and gas flow concurrently flowing downward through the packed bed while reaction takes place. Co-current downward flow provides the best hydrodynamic flow patterns with the catalyst particle sizes of interest and avoids the need of internals to keep the catalyst bed intact inside of the reactor.

The disclosed embodiments include a relatively low temperature and low pressure for the conversion of ethylene oxide to BME by reacting the ethylene oxide with hydrogen sulfide in the presence of a solid catalyst under conditions as described herein. In an embodiment, hydrogen sulfide and ethylene oxide can react in a liquid phase, wherein the liquid phase can contact the solid catalyst. As will be appreciated by one of skill in the art, and with the help of this disclosure, the relatively low temperature and low pressure employed in the disclosed process are adequate to allow for the reactants to be in a liquid phase.

According to the disclosed embodiments, ethylene oxide and hydrogen sulfide can be reacted in liquid phase at a temperature in the approximate range of from about 30° C. to about 80° C. in the presence of a heterogeneous ion exchange catalyst and at a molar ratio of hydrogen sulfide to ethylene oxide in the range of from about 9:1 to about 20:1, as previously described herein.

In an embodiment, a process for producing BME can be performed at a temperature (e.g., the reactor can be characterized by a temperature) in a range of from about 30° C. to about 80° C., alternatively from about 30° C. to about 51° C., alternatively from about 35° C. to about 75° C., or alternatively from about 40° C. to about 70° C. Generally, ion exchange resins can deactivate upon exposure to high temperatures, and as such a catalyst longevity (e.g., length of time that a catalysts does not significantly lose catalytic activity) of the heterogeneous ion exchange resin catalyst under reactor operating conditions can be extended by maintaining the temperature in the reactor under 80° C.

In an embodiment, the fixed bed of the reactor can have a weight average bed temperature (WABT) of from about 65° C. to about 70° C., alternatively from about 65.5° C. to about 69.5° C., or alternatively from about 66° C. to about 69° C. Generally, the WABT is calculated for catalyst beds that do not have a uniform catalyst distribution across the reactor (e.g., multiple catalytic zones, mixtures of catalysts and inert supports used, volumetric concentration gradient of catalyst along a catalyst fixed bed or zone thereof, etc.), wherein weight fractions of the catalysts in a particular zone are correlated with the temperature of that particular zone to contribute to the averaging of the temperatures to yield the WABT. Without wishing to be limited by theory, a temperature across the catalyst bed is expected to increase along a length of the catalyst bed, in the direction of the flow through the reactor. As will be appreciated by one of skill in the art, and with the help of this disclosure, the reaction between hydrogen sulfide and ethylene oxide to produce BME is exothermic, and since the reaction occurs primarily in the catalyst bed, the temperature of the catalyst bed (e.g., WABT) will be higher at an exit point than at an entry point. Further, as the temperature reaches a boiling point of hydrogen sulfide at the pressure inside the reactor, a portion of the hydrogen sulfide will convert to a gas phase and absorb some of the heat of reaction, thereby preventing a temperature inside the catalyst bed from getting too high and potentially damaging the catalyst. Without wanting to be limited by theory, it is believed that the enthalpy generated during the exothermic reaction of $H_2S$ with ethylene oxide is sufficient to provide the latent heat of vaporization necessary to vaporize some, most, or all of the liquid $H_2S$ after it enters the reactor. In one or more embodiments disclosed herein, the heat of vaporization of $H_2S$ is about 0.11 kcal/gm (about 198 BTU/lb) or about 3.7 kcal/mole (about 6,670 BTU/lbmole).

In an embodiment, a process for producing BME can be performed at a pressure (e.g., the reactor can be characterized by a pressure) in a range of from about 300 psig to about 500 psig, alternatively from about 350 psig to about 475 psig, or alternatively from about 400 psig to about 450 psig. In some embodiments, a process for producing BME can be performed at a pressure of about 450 psig. According to the disclosed embodiments, a pressure in the reactor has to be high enough such that the hydrogen sulfide is a liquid at the temperature inside the reactor or catalyst bed, and at the same time the pressure cannot be too high as to prevent hydrogen sulfide vaporization when the temperature increases.

In an embodiment, a weight hourly space velocity (WHSV) of the ethylene oxide can be in a range of from about 0.1 to about 1, alternatively from about 0.2 to about 0.8, or alternatively from about 0.4 to about 0.6. Generally, the weight hourly space velocity refers to a mass of reagents fed per hour divided by a mass of catalyst used in a particular reactor. The units for WHSV are (mass reagent)/(mass catalyst—hr), expressed and reported as $hr^{-1}$.

In an embodiment, a process for producing BME can further comprise converting, in the reactor, at least a portion of the hydrogen sulfide from a liquid phase to a vapor phase to absorb a heat of reaction created in the step of reacting. The reaction of ethylene oxide with hydrogen sulfide to produce BME is exothermic, and since in an embodiment the reactor does not employ an external cooling fluid or internal heat exchange elements or devices, converting at least a portion of the hydrogen sulfide from a liquid phase to a vapor phase allows for temperature control inside the reactor (e.g., adiabatic reactor). As previously described, the heat of reaction generated from the reaction with $H_2S$ and ethylene oxide is sufficient to provide the latent heat of vaporization necessary for the $H_2S$ in the reactor to transition from the liquid state into vapor. Without wishing to be limited by theory, for the reactor to operate adiabatically, or near adiabatically, the heat of reaction generated is essentially equal to the latent heat of vaporization of $H_2S$. Therefore the total enthalpy in the reactor is zero or close to zero, allowing the equilibrium between the heat of reaction and heat of vaporization to essentially control the temperature within the reactor.

In an embodiment, the step of reacting ethylene oxide with hydrogen sulfide, and the step of converting at least a portion of the hydrogen sulfide from a liquid phase to a vapor phase can occur about simultaneously.

In some embodiments, a process for producing BME can further comprise recovering a vapor phase of the hydrogen sulfide from the reactor; condensing at least a portion of the vapor phase of the hydrogen sulfide to a liquid phase; and recycling at least a portion of the liquid phase of the hydrogen sulfide to the reactor (e.g., to the hydrogen sulfide stream).

In an embodiment, an effluent stream can flow out of the reactor, wherein the effluent stream can comprise a reaction product comprising BME that is produced in the reactor by a reaction of hydrogen sulfide and ethylene oxide in liquid phase in presence of the solid catalyst (e.g., heterogeneous catalysis). For purposes of the disclosure herein, the term "reaction product" refers to any reaction products that are produced by the reaction between hydrogen sulfide and ethylene oxide, including primarily BME, and any unreacted ethylene oxide. Further, for purposes of the disclosure herein, the term "reaction product" is defined on a hydrogen sulfide-free basis, e.g., the reaction product excludes hydrogen sulfide.

In an embodiment, the effluent stream can comprise the reaction product and hydrogen sulfide. In such embodiment, the effluent stream can be subjected to a separation step to separate the hydrogen sulfide from the reaction product. For example, the effluent stream can be introduced to a high pressure stripping column wherein the hydrogen sulfide is vaporized and recovered as hydrogen sulfide vapor phase (overhead stream), which can be subsequently condensed and recycled back to the reactor. The reaction product can be recovered as a bottoms stream from the high pressure stripping column.

In an embodiment, the reaction product in the effluent can consist essentially of the BME and the TDG (e.g., the reaction product can comprise less than about 1 wt. %, less than about 0.1 wt. %, less than about 0.01 wt. %, or less than about 0.001 wt. % ethylene oxide, based on a total weight of the reaction product). In an embodiment, an effluent of the reactor (e.g., effluent stream) can comprise the reaction product, wherein the reaction product in the effluent further comprises equal to or greater than about 99 wt. %, alternatively equal to or greater than about 99.5 wt. %, or alternatively equal to or greater than about 99.9 wt. % BME (with any remainder comprising TDG and/or unreacted ethylene oxide). According to the embodiments of this disclosure, it is possible to produce a reaction product having upwards of 99 wt. % purity BME.

In an embodiment, an effluent of the reactor (e.g., effluent stream) can comprise the reaction product, wherein the reaction product in the effluent further comprises less than about 0.5 wt. %, alternatively less than about 0.25 wt. %, alternatively less than about 0.1 wt. %, alternatively less than about 0.05 wt. %, or alternatively less than about 0.01 wt. % TDG and/or unreacted ethylene oxide. TDG can form by exothermic reaction of BME with ethylene oxide. As will be appreciated by one of skill in the art, and with the help of this disclosure, TDG is generally present as an undesirable product (e.g., impurity) in reaction products from BME production processes. Without wishing to be limited by theory, the heterogeneous ion exchange resin as disclosed herein catalyzes selectively the formation of BME from ethylene oxide and hydrogen sulfide, and as such only a very low amount of undesirable products such as TDG is formed, or no amount of undesirable products such as TDG is formed.

In some embodiments, the reaction product is essentially free of TDG, e.g., the reaction product comprises no TDG. In an embodiment, the reaction product consists of, or consists essentially of, BME. In an embodiment, no TDG can be detected (e.g., by gas chromatography) in the reaction product. In an embodiment, the amount of TDG in the reaction product is 0 wt. % or 0 mol %.

In some embodiments, the reaction product is essentially free of unreacted ethylene oxide, e.g., the reaction product comprises no unreacted ethylene oxide. In an embodiment, the amount of unreacted ethylene oxide in the reaction product is 0 wt. % or 0 mol %.

In an embodiment, no detectable amount of EDT is present in the reaction product when analyzing a sample of an effluent of the reactor via gas chromatography to two decimal places for weight percent or to three decimal places for mole percent. Conventional processes for the production of BME from the reaction of ethylene oxide with hydrogen sulfide generally lead to the production of EDT, which is another undesirable product (e.g., impurity) in the reaction products, in addition to TDG.

In some embodiments, the reaction product is essentially free of EDT, e.g., the reaction product comprises no EDT. In an embodiment, the amount of EDT in the reaction product is 0.00 wt. % or 0.000 mol %.

Measurements can be taken with any gas chromatography technique known by those skilled in the art with the aid of this disclosure. Examples of suitable gas chromatography (GC) techniques include those which utilize a capillary column having a nonpolar stationary phase (e.g., 100% dimethylpolysiloxane). Using a capillary column as described allows for separation by component volatility (i.e., boiling point) only. Nonlimiting examples of capillary columns are VF-1 ms and CP-Sil 5 CB. The detector used in the GC technique may be a TCD detector or FID detector. A TCD detector can detect water and $H_2S$ in a single analysis, while FID can detect the reaction products, for example, in high purity.

For purposes of the disclosure herein, a selectivity to BME can be calculated by dividing an amount of ethylene oxide that was converted to BME in a given time period in a flow reactor by the total amount of ethylene oxide that was converted into any reaction product, including BME, over the exact same time period in the same flow reactor. In an embodiment, a process for producing BME can be characterized by a selectivity to BME of greater than about 99 wt. %, alternatively greater than about 99.5 wt. %, or alternatively greater than about 99.9 wt. %, based on a total weight of ethylene oxide that was converted to BME divided by a total weight of ethylene oxide that was converted into the reaction product. In an embodiment, the solid catalyst having weakly basic active groups can allow a conversion of the ethylene oxide with a selectivity to BME of greater than about 99 wt. %, based on a total weight of ethylene oxide that was converted to BME divided by a total weight of ethylene oxide that was converted into the reaction product. Without wishing to be limited by theory, the heterogeneous ion exchange resin having weakly basic active groups could selectively enable the formation of BME, while selectively inhibiting the formation of undesirable products such as EDT and TDG.

For purposes of the disclosure herein, a conversion of ethylene oxide to reaction products can be calculated by dividing an amount of ethylene oxide that was converted to reaction product in a given time period in a flow reactor by the total amount of ethylene oxide that was introduced to the same flow reactor, over the exact same time period. In an embodiment, the step of reacting ethylene oxide with hydrogen sulfide to produce BME can include a conversion of ethylene oxide to the reaction product that is greater than about 99 wt. %, alternatively greater than about 99.5 wt. %, or alternatively greater than about 99.9 wt. %, based on the weight of ethylene oxide that was converted to reaction product divided by the weight of ethylene oxide fed to the reactor.

In an embodiment, a process for producing BME can comprise reacting, in an adiabatic continuous flow reactor having a fixed bed containing a solid catalyst comprising a heterogeneous ion exchange resin, hydrogen sulfide and ethylene oxide in the presence of the solid catalyst to yield a reaction product comprising BME; wherein during steady state operation of the reactor, the hydrogen sulfide and the ethylene oxide can be present in a mole ratio in a range of about 9:1 to about 20:1; wherein the process can be performed at a temperature in a range of from about 30° C. to about 80° C., and a pressure of about 450 psig; wherein the heterogeneous ion exchange resin comprises a styrene-DVB copolymer with weakly basic active groups comprising alkyl amines; and wherein a selectivity to BME can be greater than about 99 wt. %, based on a total weight of ethylene oxide that was converted to BME divided by a total weight of ethylene oxide that was converted into the reaction product.

In an embodiment, a reactor system for producing BME can comprise an adiabatic continuous flow reactor; an ethylene oxide stream feeding ethylene oxide to the reactor; a hydrogen sulfide stream feeding hydrogen sulfide to the reactor; a fixed bed containing a solid catalyst placed in the reactor, wherein the solid catalyst comprises a styrene-DVB copolymer with weakly basic active groups comprising alkyl amines; and an effluent stream flowing from the reactor, wherein the effluent stream comprises a reaction product comprising BME produced in the reactor by a reaction of hydrogen sulfide and ethylene oxide in presence of the solid catalyst; wherein the hydrogen sulfide and the ethylene oxide are present in the reactor during steady state operation in a mole ratio ranging from about 9:1 to about 20:1; wherein the reactor operates at a temperature in a range of from about 30° C. to about 80° C. and a pressure of about 450 psig; wherein a conversion of ethylene oxide to the reaction product can be greater than about 99 wt. %, based on the weight of ethylene oxide that was converted to reaction product divided by the weight of ethylene oxide fed to the reactor; and wherein a selectivity to BME can be greater than about 99 wt. %, based on a total weight of ethylene oxide that was converted to BME divided by a total weight of ethylene oxide that was converted into the reaction product.

In an embodiment, a process for producing BME as disclosed herein can advantageously display improvements in one or more process characteristics when compared to conventional processes for the production of BME. In conventional processes for the production of BME, generally, continuous stirred-tank reactors are employed. In an embodiment, a PFR as disclosed herein can advantageously allow for safer operation. In an embodiment, a process for producing BME as disclosed herein can advantageously employ an adiabatic reactor (e.g., an adiabatic PFR), which is easier to operate due to no secondary heat exchange requirement (e.g., in the case of an adiabatic reactor, there is no need to cool the reactor by using energy input from outside the reactor). In an embodiment, a process for producing BME as disclosed herein can advantageously employ an adiabatic reactor (e.g., an adiabatic PFR), which is smaller (i.e., requires a smaller footprint) than a CSTR to achieve the same conversion. In an embodiment, a process for producing BME as disclosed herein can advantageously employ an adiabatic reactor (e.g., an adiabatic PFR), which has lower capital and operating costs compared to a comparable CSTR reactor.

In an embodiment, a process for producing BME as disclosed herein can advantageously allow for an increased selectivity of ethylene oxide to BME (of about 99%), when compared to other conventional processes for the production of BME (typically about 92%). In an embodiment, a process for producing BME as disclosed herein can advantageously allow for near quantitative conversion of ethylene oxide to reaction products (of about 99%) when compared a conventional processes for the production of BME.

In an embodiment, a process for producing BME as disclosed herein can advantageously employ a solid catalyst (as opposed to a liquid catalyst or liquid initiator used in conventional processes for the production of BME), and as such the catalyst remains in the reactor and is not removed with the products, as is the case with liquid catalysts and initiators, which would further require an additional separation step to recover the products from the liquid catalysts and/or initiators.

In an embodiment, a process for producing BME as disclosed herein can advantageously eliminate the need for using a liquid caustic initiator for the reaction between ethylene oxide and hydrogen sulfide by using a solid basic catalyst.

In an embodiment, a process for producing BME as disclosed herein can advantageously allow for a higher rate of production (e.g., higher BME output) owing to a higher heat exchanging capacity of the reactor.

In an embodiment, a process for producing BME as disclosed herein can advantageously allow for producing a significantly lower amount of BME impurities (less than about 0.5 wt. %), such as TDG, EDT, or both, when compared to other conventional processes for the production of BME, which can produce 5-7 wt. % impurities that have to be separated and disposed of. As will be appreciated by one of skill in the art, and with the help of this disclosure, EDT has an unpleasant odor, and as such there are certain difficulties associated with EDT separation and disposal. Additional advantages of the systems and/or methods for the production of a BME as disclosed herein can be apparent to one of skill in the art viewing this disclosure and include but are not limited to a smaller reactor size, a smaller reactor footprint, lower capital costs, and lower operating costs.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

The following general experimental procedure was used for all examples, unless otherwise indicated.

Producing beta-mercaptoethanol (BME) was studied for various experimental conditions, such as catalyst, temperature, and reactant ratios. More specifically, the synthesis of BME was investigated for two different catalysts, AMBERLYST® A21 resin and LEWATIT® MP 62 resin.

The BME synthesis reaction from ethylene oxide and $H_2S$ is highly exothermic:

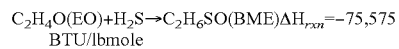

$C_2H_4O(EO)+H_2S \rightarrow C_2H_6SO(BME) \Delta H_{rxn}=-75,575$ BTU/lbmole

$C_2H_6SO(BME)+C_2H_4O(EO) \rightarrow (C_2H_5OH)_2S(TDG)$ $\Delta H_{rxn}=-75,870$ BTU/lbmole BME was produced in a fixed bed catalytic flow reactor operating in downflow. The reactor was a 1 inch inner diameter stainless steel jacketed reactor. The catalyst was either AMBERLYST® A21 resin or LEWATIT® MP 62 resin. Temperatures were controlled using a 50/50 glycol/water mixture flowing in upflow through the jacket. The glycol/water mixture temperature was controlled using an external Lauda RK20 constant temperature bath (of approximately 5 gallons).

During adiabatic experiments with the LEWATIT® MP 62 resin catalyst, there was no temperature control. The jacket temperature was raised sufficiently to initiate reaction, and then the flow of heat transfer fluid to the external jacket was stopped.

The catalyst packing had three equal zones (by volume): a top zone, a middle zone, and a bottom zone. The top zone was ⅔ chemically inert solid diluent (ALUNDUM® Alumina) and one-third catalyst by volume. The middle zone was ½ catalyst and ½ inert solid diluent (ALUNDUM® Alumina), again by volume. The bottom zone was all catalyst.

The ethylene oxide and hydrogen sulfide ($H_2S$) were fed independently, and each flowrate was controlled using a Brooks mass flow controller. The two feeds were combined prior to entering the reactor and mixed in a static mixer. Static mixing was achieved by passing the feed through 2 inches of glass beads. There was a thermocouple in the reactor inlet (about 5 inches above the catalyst bed) just downstream of the static mixer. The temperature measured by this thermocouple stayed at ambient temperature throughout all of the experiments.

Product analysis was conducted using a HP-6890 gas chromatograph (GC) equipped with a thermal conductivity detector. This method allows for quantification of crude BME, water, and $H_2S$ all in one analysis. On-line product samples were routed directly to the GC from the reactor effluent. The GC was equipped with a 30 m×0.32 mm 4.0 μm film CP-Sil CB column. The initial temperature was 35° C. with a 5 min hold time and was ramped to a final temperature of 260° C. at a rate of 10° C./min with a 10 min hold time. The carrier gas was helium at a flow rate of 1.0 mL/min. The thermal conductivity (TCD) response factors used were as follows: ethylene oxide 0.58, $H_2S$ 0.89, BME 0.73, thiodiglycol (TDG) 0.75, $H_2O$ 0.55, and ethanedithiol (EDT) 0.75.

The catalysts as received were about 50 wt. % water. The AMBERLYST® A21 resin catalyst was dried using flowing methanol at 40° C. However, this procedure resulted simply in displacement of water with methanol to a large extent. Thus, there was methanol in the effluent from the reactors for most of the course of the experimental work, and some of this methanol was still present in the LEWATIT® MP 62 resin experiments. The LEWATIT® MP 62 resin was dried using flowing nitrogen at 55° C. This drying procedure was not hot enough to remove all of the water from the catalyst, so there was a considerable amount of water in the reactor effluent at the start of the LEWATIT® MP 62 resin experiments.

Example 1

The reaction of ethylene oxide with hydrogen sulfide in the presence of AMBERLYST® A21 resin catalyst was investigated for various hydrogen sulfide ($H_2S$) to ethylene oxide (EO) molar ratios, and the experimental conditions are displayed in Table 1.

TABLE 1

| Sample # | Catalyst grams | $H_2S$/EO mole ratio | Press psig | EO gms/min | $H_2S$ gms/min | WHSV hr$^{-1}$ | LHSV hr$^{-1}$ | Z#1 Top ° C. | Z#2 Mid ° C. | Z#3 Btm ° C. |
|---|---|---|---|---|---|---|---|---|---|---|
| AMBERLYST ® A21 resin catalyst + ALUNDUM ® Alumina: 60 ml catalyst/50 ml ALUNDUM ® Alumina | | | | | | | | | | |
| 1 | 36.7 | 8.6 | 450 | 0.25 | 1.7 | 0.41 | 0.22 | 59 | 52 | 50 |
| 2 | 36.7 | 8.6 | 450 | 0.25 | 1.7 | 0.41 | 0.22 | 59 | 52 | 50 |
| 3 | 36.7 | 8.6 | 450 | 0.25 | 1.7 | 0.41 | 0.22 | 62 | 53 | 52 |
| 4 | 36.7 | 8.6 | 450 | 0.25 | 1.7 | 0.41 | 0.22 | 65 | 55 | 54 |
| 5 | 36.7 | 8.6 | 450 | 0.25 | 1.7 | 0.41 | 0.22 | 64 | 55 | 53 |
| 6 | 36.7 | 8.6 | 450 | 0.25 | 1.7 | 0.41 | 0.22 | 81 | 57 | 56 |
| 7 | 36.7 | 8.6 | 450 | 0.25 | 1.7 | 0.41 | 0.22 | 72 | 58 | 56 |
| 8 | 36.7 | 10.8 | 450 | 0.25 | 2.1 | 0.41 | 0.22 | 63 | 58 | 56 |
| 9 | 36.7 | 10.8 | 450 | 0.25 | 2.1 | 0.41 | 0.22 | 66 | 58 | 56 |
| 10 | 36.7 | 7.8 | 450 | 0.25 | 1.5 | 0.41 | 0.22 | 91 | 56 | 56 |
| 11 | 36.7 | 7.8 | 450 | 0.25 | 1.5 | 0.41 | 0.22 | 73 | 57 | 56 |
| 12 | 36.7 | 7.8 | 450 | 0.25 | 1.5 | 0.41 | 0.22 | 72 | 57 | 56 |
| 13 | 36.7 | 6.5 | 450 | 0.25 | 1.2 | 0.41 | 0.22 | 78 | 56 | 56 |
| 14 | 36.7 | 6.5 | 450 | 0.25 | 1.2 | 0.41 | 0.22 | 67 | 57 | 56 |
| 15 | 36.7 | 5.6 | 450 | 0.25 | 1.1 | 0.41 | 0.22 | 71 | 57 | 56 |
| 16 | 36.7 | 5.6 | 450 | 0.25 | 1.1 | 0.41 | 0.22 | 71 | 57 | 56 |

Data were collected first as rate vs. temperature at fixed pressure and fixed hydrogen sulfide to ethylene oxide molar ratios (for samples 1 through 7) and then at fixed temperature (56° C. outlet) and varying $H_2S$:EO mole ratios (for samples 8 through 16). The space velocity was calculated based upon the EO feed rate. The results for samples 1 through 16 were analyzed as previously described, and the resulting data based on wt. % are displayed in Table 2 and the resulting data based on mol % are displayed in Table 3.

TABLE 2

| Sample # | $H_2S$ Wt. % | water Wt. % | MeOH Wt. % | EO Wt. % | Unidentified Wt. % | BME Wt. % | EDT Wt. % | TDG Wt. % | EO Conv Wt. % | BME Conv Wt. % | EO to BME Selectivity Wt. % |
|---|---|---|---|---|---|---|---|---|---|---|---|
| AMBERLYST ® A21 resin catalyst + ALUNDUM ® Alumina: 60 ml catalyst/50 ml ALUNDUM ® Alumina | | | | | | | | | | | |
| 1 | 45.3 | 0.00 | 0.32 | 2.5 | 0.00 | 32.7 | 0.0 | 0.00 | 88.4 | 100.0 | 88.4 |
| 2 | 52.8 | 0.70 | 0.29 | 0.32 | 0.01 | 2796 | 0.0 | 0.09 | 98.1 | 99.6 | 97.7 |
| 3 | 49.5 | 0.21 | 0.05 | 0.27 | 0.06 | 32.1 | 0.0 | 0.23 | 98.6 | 99.1 | 97.7 |
| 4 | 56.8 | 0.35 | 0.03 | 0.24 | 0.01 | 25.2 | 0.0 | 0.39 | 98.4 | 98.5 | 96.9 |
| 5 | 55.7 | 0.00 | 0.02 | 0.13 | 0.01 | 2677 | 0.0 | 0.41 | 99.2 | 98.5 | 97.7 |
| 6 | 61.5 | 0.00 | 0.01 | 0.06 | 0.02 | 22.1 | 0.0 | 0.28 | 99.5 | 98.7 | 98.3 |
| 7 | 63.4 | 0.33 | 0.01 | 0.03 | 0.01 | 20.2 | 0.0 | 0.18 | 99.8 | 99.1 | 98.8 |
| 8 | 77.0 | 0.00 | 0.26 | 0.02 | 0.00 | 9.4 | 0.0 | 0.02 | 99.7 | 99.8 | 99.5 |
| 9 | 74.1 | 0.00 | 0.09 | 0.01 | 0.00 | 12.0 | 0.0 | 0.07 | 99.8 | 99.4 | 99.2 |
| 10 | 73.2 | 0.00 | 0.05 | 0.01 | 0.00 | 12.7 | 0.0 | 0.11 | 99.9 | 99.2 | 99.1 |
| 11 | 69.9 | 0.00 | 0.03 | 0.01 | 0.00 | 15.4 | 0.0 | 0.15 | 99.9 | 99.0 | 99.0 |
| 12 | 66.4 | 0.00 | 0.02 | 0.01 | 0.00 | 18.4 | 0.0 | 0.07 | 99.9 | 99.6 | 99.6 |
| 13 | 68.6 | 0.00 | 0.02 | 0.01 | 0.01 | 16.6 | 0.0 | 0.06 | 99.9 | 99.6 | 99.5 |
| 14 | 64.7 | 0.00 | 0.01 | 0.01 | 0.01 | 19.8 | 0.0 | 0.07 | 99.9 | 99.6 | 99.6 |
| 15 | 63.6 | 0.00 | 0.02 | 0.01 | 0.01 | 20.7 | 0.0 | 0.05 | 99.9 | 99.7 | 99.6 |
| 16 | 64.0 | 0.00 | 0.03 | 0.01 | 0.01 | 20.1 | 0.0 | 0.11 | 99.9 | 99.4 | 99.4 |

Conv = conversion

TABLE 3

| Sample # | $H_2S$ Mol % | water Mol % | MeOH Mol % | EO Mol % | Unidentified Mol % | BME Mol % | EDT Mol % | TDG Mol % | EO Conv Mol % | BME Conv Mol % | EO to BME Selectivity Mol % |
|---|---|---|---|---|---|---|---|---|---|---|---|
| AMBERLYST ® A21 resin catalyst + ALUNDUM ® Alumina: 60 ml catalyst/50 ml ALUNDUM ® Alumina ||||||||||||
| 1 | 73.4 | 0.00 | 0.39 | 3.1 | 0.00 | 23.1 | 0.0 | 0.00 | 88.0 | 100.0 | 88.0 |
| 2 | 79.1 | 1.98 | 0.32 | 0.37 | 0.01 | 18.2 | 0.0 | 0.04 | 98.0 | 99.5 | 97.5 |
| 3 | 77.0 | 0.63 | 0.06 | 0.32 | 0.07 | 21.8 | 0.0 | 0.10 | 98.6 | 98.8 | 97.4 |
| 4 | 82.6 | 0.97 | 0.03 | 0.27 | 0.01 | 16.0 | 0.0 | 0.16 | 98.4 | 98.0 | 96.4 |
| 5 | 82.4 | 0.00 | 0.02 | 0.15 | 0.01 | 17.2 | 0.0 | 0.17 | 99.1 | 98.0 | 97.1 |
| 6 | 86.3 | 0.00 | 0.01 | 0.07 | 0.02 | 13.5 | 0.0 | 0.11 | 99.5 | 98.3 | 97.8 |
| 7 | 86.9 | 0.86 | 0.01 | 0.03 | 0.01 | 12.1 | 0.0 | 0.07 | 99.7 | 98.8 | 98.5 |
| 8 | 94.7 | 0.00 | 0.24 | 0.02 | 0.00 | 5.0 | 0.0 | 0.01 | 99.7 | 99.8 | 99.5 |
| 9 | 93.3 | 0.00 | 0.08 | 0.01 | 0.00 | 6.6 | 0.0 | 0.02 | 99.8 | 99.3 | 99.1 |
| 10 | 92.9 | 0.00 | 0.04 | 0.01 | 0.00 | 7.0 | 0.0 | 0.04 | 99.9 | 98.9 | 98.8 |
| 11 | 91.2 | 0.00 | 0.03 | 0.01 | 0.00 | 8.7 | 0.0 | 0.06 | 99.9 | 98.7 | 98.7 |
| 12 | 89.2 | 0.00 | 0.02 | 0.01 | 0.00 | 10.8 | 0.0 | 0.03 | 99.9 | 99.5 | 99.4 |
| 13 | 90.4 | 0.00 | 0.02 | 0.01 | 0.01 | 9.5 | 0.0 | 0.02 | 99.9 | 99.5 | 99.4 |
| 14 | 88.2 | 0.00 | 0.01 | 0.01 | 0.01 | 11.8 | 0.0 | 0.03 | 99.9 | 99.5 | 99.4 |
| 15 | 87.5 | 0.00 | 0.02 | 0.01 | 0.01 | 12.4 | 0.0 | 0.02 | 99.9 | 99.6 | 99.5 |
| 16 | 87.8 | 0.00 | 0.03 | 0.01 | 0.01 | 12.1 | 0.0 | 0.04 | 99.9 | 99.2 | 99.2 |

Conv = conversion

Example 2

The reaction of ethylene oxide with hydrogen sulfide in the presence of LEWATIT® MP 62 resin catalyst was investigated for various hydrogen sulfide to ethylene oxide molar ratios, and the experimental conditions are displayed in Table 4. The reactor was operated with external cooling (analogous to the data in Example 1).

TABLE 4

| Sample # | Catalyst grams | $H_2S$/EO mole ratio | Press psig | EO gms/min | WHSV $hr^{-1}$ | LHSV $hr^{-1}$ | Z#1 Top T ° C. | Z#2 Mid T ° C. | Z#3 Btm T ° C. |
|---|---|---|---|---|---|---|---|---|---|
| LEWATIT ® MP 62 resin catalyst + ALUNDUM ® Alumina: 56 ml catalyst/54 ml ALUNDUM ® Alumina ||||||||||
| 17 | 28.1 | 8.6 | 450 | 0.25 | 0.53 | 0.22 | 62 | 57 | 56 |
| 18 | 28.1 | 8.6 | 450 | 0.25 | 0.53 | 0.22 | 60 | 56 | 56 |
| 19 | 28.1 | 8.6 | 450 | 0.25 | 0.53 | 0.22 | 61 | 57 | 56 |
| 20 | 28.1 | 8.6 | 450 | 0.25 | 0.53 | 0.22 | 73 | 57 | 56 |
| 21 | 28.1 | 8.6 | 450 | 0.25 | 0.53 | 0.22 | 63 | 57 | 56 |
| 22 | 28.1 | 8.6 | 450 | 0.25 | 0.53 | 0.22 | 71 | 57 | 56 |
| 23 | 28.1 | 10.8 | 450 | 0.25 | 0.53 | 0.22 | 70 | 57 | 56 |
| 24 | 28.1 | 10.8 | 450 | 0.25 | 0.53 | 0.22 | 67 | 57 | 56 |
| 25 | 28.1 | 7.8 | 450 | 0.25 | 0.53 | 0.22 | 70 | 57 | 56 |
| 26 | 28.1 | 7.8 | 450 | 0.25 | 0.53 | 0.22 | 72 | 57 | 56 |
| 27 | 28.1 | 6.0 | 450 | 0.25 | 0.53 | 0.22 | 58 | 56 | 56 |
| 28 | 28.1 | 6.0 | 450 | 0.25 | 0.53 | 0.22 | 62 | 56 | 56 |
| 29 | 28.1 | 4.3 | 450 | 0.25 | 0.53 | 0.22 | 60 | 56 | 56 |
| 30 | 28.1 | 4.3 | 450 | 0.25 | 0.53 | 0.22 | 58 | 56 | 56 |

Data were collected first as rate vs. temperature at fixed pressure and fixed hydrogen sulfide to ethylene oxide molar ratios (for samples 17 through 22) and then at fixed temperature (56° C. outlet) and varying $H_2S$:EO mole ratios (for samples 23 through 30). The space velocity was calculated based upon the EO feed rate. The results for samples 17 through 30 were analyzed as previously described, and the resulting data based on wt. % are displayed in Table 5 and the resulting data based on mol % are displayed in Table 6.

TABLE 5

| Sample # | H$_2$S Wt. % | water Wt. % | MeOH Wt. % | EO Wt. % | Unidentified Wt. % | BME Wt. % | EDT Wt. % | TDG Wt. % | EO Conv Wt. % | BME Conv Wt. % | EO to BME Selectivity Wt. % |
|---|---|---|---|---|---|---|---|---|---|---|---|
| LEWATIT® MP 62 resin catalyst + ALUNDUM® Alumina: 56 ml catalyst/54 ml ALUNDUM® Alumina | | | | | | | | | | | |
| 17 | 46.5 | 4.8 | 0.151 | 0.019 | 0.000 | 27.6 | 0.0 | 0.00 | 99.9 | 100.0 | 99.9 |
| 18 | 53.7 | 1.3 | 0.026 | 0.014 | 0.008 | 26.8 | 0.0 | 0.12 | 99.9 | 99.5 | 99.4 |
| 19 | 59.3 | 0.4 | 0.012 | 0.011 | 0.006 | 23.3 | 0.0 | 0.36 | 99.9 | 98.4 | 98.4 |
| 20 | 64.4 | 0.21 | 0.010 | 0.008 | 0.007 | 19.4 | 0.0 | 0.23 | 99.9 | 98.8 | 98.7 |
| 21 | 65.9 | 0.99 | 0.006 | 0.007 | 0.008 | 17.3 | 0.0 | 0.20 | 99.9 | 98.8 | 98.8 |
| 22 | 67.6 | 0.00 | 0.008 | 0.008 | 0.007 | 17.2 | 0.0 | 0.16 | 99.9 | 99.0 | 99.0 |
| 23 | 73.1 | 0.19 | 0.128 | 0.010 | 0.000 | 12.4 | 0.0 | 0.04 | 99.9 | 99.7 | 99.5 |
| 24 | 74.3 | 0.00 | 0.027 | 0.000 | 0.000 | 11.8 | 0.0 | 0.08 | 100.0 | 99.3 | 99.3 |
| 25 | 72.9 | 0.00 | 0.010 | 0.000 | 0.000 | 12.9 | 0.0 | 0.21 | 100.0 | 98.4 | 98.4 |
| 26 | 71.8 | 0.00 | 0.015 | 0.000 | 0.000 | 13.5 | 0.0 | 0.34 | 100.0 | 97.6 | 97.6 |
| 27 | 69.3 | 0.00 | 0.010 | 0.000 | 0.000 | 15.8 | 0.0 | 0.22 | 100.0 | 98.6 | 98.6 |
| 28 | 67.3 | 0.00 | 0.009 | 0.000 | 0.005 | 17.5 | 0.0 | 0.15 | 100.0 | 99.1 | 99.1 |
| 29 | 65.8 | 0.00 | 0.005 | 0.000 | 0.006 | 18.8 | 0.0 | 0.10 | 100.0 | 99.4 | 99.4 |
| 30 | 63.6 | 0.00 | 0.000 | 0.000 | 0.000 | 20.6 | 0.0 | 0.07 | 100.0 | 99.7 | 99.7 |

Conv = conversion

TABLE 6

| Sample # | H$_2$S Mol % | water Mol % | MeOH Mol % | EO Mol % | Unidentified Mol % | BME Mol % | EDT Mol % | TDG Mol % | EO Conv Mol % | BME Conv Mol % | EO to BME Selectivity Mol % |
|---|---|---|---|---|---|---|---|---|---|---|---|
| LEWATIT® MP 62 resin catalyst + ALUNDUM® Alumina: 56 ml catalyst/54 ml ALUNDUM® Alumina | | | | | | | | | | | |
| 17 | 68.7 | 13.3 | 0.237 | 0.022 | 0.000 | 17.8 | 0.0 | 0.00 | 99.9 | 100.0 | 99.9 |
| 18 | 79.1 | 3.5 | 0.041 | 0.016 | 0.006 | 17.2 | 0.0 | 0.05 | 99.9 | 99.4 | 99.3 |
| 19 | 84.4 | 0.96 | 0.018 | 0.012 | 0.005 | 14.5 | 0.0 | 0.14 | 99.9 | 98.0 | 97.9 |
| 20 | 87.8 | 0.55 | 0.014 | 0.009 | 0.005 | 11.6 | 0.0 | 0.09 | 99.9 | 98.5 | 98.4 |
| 21 | 87.4 | 2.5 | 0.009 | 0.007 | 0.006 | 10.0 | 0.0 | 0.07 | 99.9 | 98.5 | 98.4 |
| 22 | 89.9 | 0.0 | 0.011 | 0.009 | 0.005 | 10.0 | 0.0 | 0.06 | 99.9 | 98.8 | 98.7 |
| 23 | 92.5 | 0.45 | 0.173 | 0.010 | 0.000 | 6.8 | 0.0 | 0.01 | 99.9 | 99.6 | 99.5 |
| 24 | 93.4 | 0.00 | 0.036 | 0.000 | 0.000 | 6.5 | 0.0 | 0.03 | 100.0 | 99.1 | 99.1 |
| 25 | 92.8 | 0.00 | 0.013 | 0.000 | 0.000 | 7.1 | 0.0 | 0.07 | 100.0 | 98.0 | 98.0 |
| 26 | 92.3 | 0.00 | 0.020 | 0.000 | 0.000 | 7.6 | 0.0 | 0.12 | 100.0 | 96.9 | 96.9 |
| 27 | 90.9 | 0.00 | 0.014 | 0.000 | 0.000 | 9.0 | 0.0 | 0.08 | 100.0 | 98.2 | 98.2 |
| 28 | 89.7 | 0.00 | 0.012 | 0.000 | 0.003 | 10.2 | 0.0 | 0.06 | 100.0 | 98.9 | 98.9 |
| 29 | 88.9 | 0.00 | 0.007 | 0.000 | 0.004 | 11.1 | 0.0 | 0.04 | 100.0 | 99.3 | 99.3 |
| 30 | 87.6 | 0.00 | 0.000 | 0.000 | 0.000 | 12.4 | 0.0 | 0.03 | 100.0 | 99.6 | 99.6 |

Conv = conversion

Example 3

The reaction of ethylene oxide with hydrogen sulfide in the presence of LEWATIT® MP 62 resin catalyst was investigated for various hydrogen sulfide to ethylene oxide molar ratios, and the experimental conditions are displayed in Table 7. The reactor was operated adiabatically, with no external heat transfer.

TABLE 7

| Sample # | Catalyst grams | H$_2$S/EO mole ratio | Press psig | EO gms/min | H$_2$S gms/min | WHSV hr$^{-1}$ | LHSV hr$^{-1}$ | Z#1 Top °C. | Z#2 Mid °C. | Z#3 Btm °C. |
|---|---|---|---|---|---|---|---|---|---|---|
| LEWATIT® MP 62 resin catalyst + ALUNDUM® Alumina: 56 ml catalyst/54 ml ALUNDUM® Alumina Adiabatic | | | | | | | | | | |
| 31 | 28.1 | 9.9 | 450 | 0.25 | 1.9 | 0.53 | 0.22 | 82 | 56 | 55.0 |
| 32 | 28.1 | 9.9 | 450 | 0.25 | 1.9 | 0.53 | 0.22 | 72 | 53 | 45.0 |
| 33 | 28.1 | 9.9 | 450 | 0.25 | 1.9 | 0.53 | 0.22 | 71 | 42 | 35.0 |
| 34 | 28.1 | 8.6 | 450 | 0.25 | 1.7 | 0.53 | 0.22 | 70 | 37 | 33.0 |
| 35 | 28.1 | 8.6 | 450 | 0.25 | 1.7 | 0.53 | 0.22 | 77 | 36 | 33.0 |
| 35 | 28.1 | 8.6 | 450 | 0.25 | 1.7 | 0.53 | 0.22 | 76 | 39 | 33.0 |
| 37 | 28.1 | 7.8 | 450 | 0.25 | 1.5 | 0.53 | 0.22 | 68 | 37 | 34.0 |
| 38 | 28.1 | 7.8 | 450 | 0.25 | 1.5 | 0.53 | 0.22 | 64 | 36 | 34.0 |
| 39 | 28.1 | 6.9 | 450 | 0.25 | 1.3 | 0.53 | 0.22 | 68 | 37 | 34.0 |

Data were collected first as rate vs. temperature at fixed pressure and fixed hydrogen sulfide to ethylene oxide molar ratios (for samples 17 through 22) and then at fixed temperature (56° C. outlet) and varying $H_2S$:EO mole ratios (for samples 23 through 30). The space velocity was calculated based upon the EO feed rate. The results for samples 31 through 39 were analyzed as previously described, and the resulting data based on wt. % are displayed in Table 8 and the resulting data based on mol % are displayed in Table 9.

not remove all the moisture, there could be some moisture present initially during start-up; however, such moisture would be preferable to residual alcohols.

Process Conditions for BME Synthesis from Ethylene Oxide Using Basic Catalysts. The conditions that appeared most favorable were: weight average bed temperature (WAT) of 65-70° C.; pressure of at least 450 psig, ethylene oxide weight hourly space velocity of 0.5 to 0.6, and $H_2S$/EO mole ratio of 9:1 (or greater). $H_2S$/EO mole ratios

TABLE 8

| Sample # | $H_2S$ Wt. % | water Wt. % | MeOH Wt. % | EO Wt. % | Unidentifed Wt. % | BME Wt. % | EDT Wt. % | Unidentifed Wt. % | TDG Wt. % | EO Conv Wt. % | BME Conv Wt. % | EO to BME Selectivity Wt. % |
|---|---|---|---|---|---|---|---|---|---|---|---|---|
| LEWATIT ® MP 62 resin catalyst + ALUNDUM ® Alumina: 56 ml catalyst/54 ml ALUNDUM ® Alumina Adiabatic |||||||||||||
| 31 | 79.0 | 0.18 | 0.05 | 0.00 | 0.00 | 7.8 | 0.00 | 0.00 | 0.02 | 100.0 | 99.7 | 99.7 |
| 32 | 74.9 | 0.00 | 0.03 | 0.00 | 0.00 | 11.4 | 0.00 | 0.00 | 0.07 | 100.0 | 99.4 | 99.4 |
| 33 | 72.2 | 0.00 | 0.01 | 0.00 | 0.00 | 13.6 | 0.00 | 0.00 | 0.16 | 100.0 | 98.9 | 98.9 |
| 34 | 72.7 | 0.00 | 0.01 | 0.01 | 0.00 | 13.0 | 0.01 | 0.01 | 0.20 | 99.9 | 98.4 | 98.3 |
| 35 | 72.3 | 0.00 | 0.00 | 0.01 | 0.00 | 13.3 | 0.01 | 0.00 | 0.21 | 99.9 | 98.4 | 98.3 |
| 35 | 72.0 | 0.00 | 0.01 | 0.01 | 0.00 | 13.5 | 0.01 | 0.01 | 0.36 | 99.9 | 97.3 | 97.2 |
| 37 | 70.0 | 0.76 | 0.00 | 0.01 | 0.00 | 14.0 | 0.00 | 0.00 | 0.52 | 99.9 | 96.5 | 96.4 |
| 38 | 70.4 | 0.00 | 0.00 | 0.01 | 0.01 | 14.7 | 0.01 | 0.00 | 0.51 | 99.9 | 96.6 | 96.5 |
| 39 | 69.5 | 0.62 | 0.01 | 0.01 | 0.00 | 14.4 | 0.04 | 0.01 | 0.51 | 99.8 | 96.3 | 96.2 |

Conv = conversion

TABLE 9

| Sample # | $H_2S$ Mol % | water Mol % | MeOH Mol % | EO Mol % | Unidentifed Mol % | BME Mol % | EDT Mol % | Unidentifed Mol % | TDG Mol % | EO Conv Mol % | BME Conv Mol % | EO to BME Selectivity Mol % |
|---|---|---|---|---|---|---|---|---|---|---|---|---|
| LEWATIT ® MP 62 resin catalyst + ALUNDUM ® Alumina: 56 ml catalyst/54 ml ALUNDUM ® Alumina Adiabatic |||||||||||||
| 31 | 95.4 | 0.41 | 0.04 | 0.00 | 0.00 | 4.1 | 0.00 | 0.00 | 0.01 | 100.0 | 99.6 | 99.6 |
| 32 | 93.7 | 0.0 | 0.02 | 0.00 | 0.00 | 6.2 | 0.00 | 0.00 | 0.02 | 100.0 | 99.3 | 99.3 |
| 33 | 92.4 | 0.0 | 0.01 | 0.00 | 0.00 | 7.6 | 0.00 | 0.00 | 0.06 | 100.0 | 98.5 | 98.5 |
| 34 | 92.7 | 0.0 | 0.01 | 0.01 | 0.00 | 7.2 | 0.00 | 0.00 | 0.07 | 99.9 | 98.0 | 97.9 |
| 35 | 92.5 | 0.0 | 0.00 | 0.01 | 0.00 | 7.4 | 0.01 | 0.00 | 0.07 | 99.9 | 98.0 | 97.9 |
| 35 | 92.3 | 0.0 | 0.01 | 0.01 | 0.00 | 7.5 | 0.01 | 0.00 | 0.13 | 99.9 | 96.6 | 96.5 |
| 37 | 90.1 | 1.8 | 0.00 | 0.01 | 0.00 | 7.9 | 0.00 | 0.00 | 0.19 | 99.9 | 95.4 | 95.3 |
| 38 | 91.5 | 0.0 | 0.00 | 0.01 | 0.01 | 8.3 | 0.01 | 0.00 | 0.18 | 99.9 | 95.6 | 95.5 |
| 39 | 90.1 | 1.5 | 0.01 | 0.01 | 0.00 | 8.1 | 0.02 | 0.01 | 0.19 | 99.8 | 95.4 | 95.2 |

Conv = conversion

Referring to the data presented in the Examples 2 and 3, the results of running the BME synthesis reaction in the presence of the two different catalysts and under different conditions is now discussed herein.

/Catalyst Packing and Preparation. Both AMBERLYST® A21 resin and LEWATIT® MP 62 resin worked well for the BME synthesis. The catalyst packing with ALUNDUM® Alumina diluent was found to perform in a satisfactory manner.

The catalyst should be dried prior to first usage. The catalyst (as received) can be as much as 50 wt. % water. In addition, ion exchange catalysts should not be exposed to prolonged temperatures in excess of 80° C., as the catalysts can lose activity. Completely anhydrous conditions prior to start-up cannot be achieved by simply sparging with heated nitrogen. Heating catalysts in flowing nitrogen for 20-24 hours at 60-65° C. could help condition catalysts prior to use in the reactor for BME synthesis. Moisture removal using flowing alcohol (methanol or isopropanol) leaves undesirable residual alcohols. Should the nitrogen drying procedure higher than 9:1 resulted in less heavies (EDT and TDG) production. Pressure and space velocities were not varied during the experiments.

Product Composition and Ethylene Oxide Conversion. Ethylene oxide conversion was essentially 100%. Virtually all the EO was consumed during the reaction. Products of reaction (at 9:1 or higher $H_2S$/EO mole ratios) were BME and TDG only. By comparison with conventional BME synthesis processes that could yield a heavies production of about 5-7 wt. %, the data in Examples 2 and 3 indicate that for 9:1 or higher $H_2S$/EO mole ratios, heavies production was well below 0.5 wt. %.

Effect of $H_2S$/EO Mole Ratio. Conversion of EO was quantitative at all mole ratios that were tested. Selectivity to BME was greater than 99% for $H_2S$/EO mole ratios in excess of 9:1. There was measurable EDT formation at mole ratios of 8:1 or less. Two additional unidentified products were also detected at mole ratios of less than 8:1 during the adiabatic experiments (Example 3). There was water in the reactor effluent concurrent with the detection of EDT, as expected (Sample 39 in Example 3).

Unidentified Peaks. While no efforts were made to identify the minor components produced at lower $H_2S/EO$ mole ratios, possibilities include ethylene sulfide and its derivatives. In addition, since there was always some methanol in the feedstock, some of the unidentified peaks could have been products of reaction of methanol. At $H_2S/EO$ mole ratios of greater than 8:1, these unidentified peaks were not present.

Utility for BME Synthesis. The selectivity of EO to BME was improved from about 92% for conventional BME synthesis processes to >99% for 9:1 or higher $H_2S/EO$ mole ratios. As a consequence of this improved selectivity, the $H_2S$ usage needed for BME synthesis could be reduced by about 5-7%, when compared to conventional BME synthesis processes. Also, heavies production could be curtailed by more than 90%, when compared to conventional BME synthesis processes.

Example 4

The activation energy for BME synthesis from ethylene oxide and hydrogen sulfide was also investigated in the presence of the LEWATIT® MP 62 resin catalyst. The activation energy for BME synthesis on LEWATIT® MP 62 resin catalyst was found to be extremely low.

FIG. 1 displays an Arrhenius plot of activation energies for LEWATIT® MP-62 catalyzed BME synthesis from ethylene oxide and $H_2S$. The Arrhenius plot of FIG. 1 is a plot of log mole % BME vs. inverse temperature. Arrhenius rate expressions for BME synthesis and related reactions are shown in Equations 1A, 1B and 1C:

$$\log \text{mole \% EO} = -2.783 - 1245.4 * 1/T(1/R); R^2 = 0.01 \quad (1A)$$

$$\log \text{mole \% BME} = -0.718 + 1710.8 * 1/T(1/R); R^2 = 0.551 \quad (1B)$$

$$\log \text{mole \% TDG} = -22.682 + 12753.6 * 1/T(1/R); R^2 = 0.424 \quad (1C)$$

From the R squared value in Equation 1A, it can be readily inferred that temperature has almost no effect on EO conversion, with temperatures above 50° C. resulting in essentially 100% EO conversion.

Additional Description

Embodiments of methods for treater regeneration have been described. The following are a first set of nonlimiting, specific embodiments in accordance with the present disclosure:

Embodiment 1 is a process comprising reacting, in a reactor having a fixed bed containing a solid catalyst comprising a heterogeneous ion exchange resin, hydrogen sulfide and ethylene oxide in the presence of the solid catalyst to yield a reaction product comprising beta-mercaptoethanol, wherein during steady state operation of the reactor, the hydrogen sulfide and the ethylene oxide are present in a mole ratio in a range of about 9:1 to about 20:1.

Embodiment 2 is the process of embodiment 1, further comprising converting, in the reactor, at least a portion of the hydrogen sulfide from a liquid phase to a vapor phase to absorb a heat of reaction created in the step of reacting.

Embodiment 3 is the process of embodiment 2, wherein the step of reacting and the step of converting occur about simultaneously.

Embodiment 4 is the process of any of embodiments 1 to 3, wherein no internal and/or external cooling source is used to cool the reactor.

Embodiment 5 is the process of any of embodiments 1 to 4, wherein an effluent of the reactor comprises the reaction product, wherein the reaction product in the effluent further comprises less than about 0.5 wt. % thiodiglycol.

Embodiment 6 is the process of embodiment 5, wherein the reaction product in the effluent consists essentially of the beta-mercaptoethanol and the thiodiglycol.

Embodiment 7 is the process of any of embodiments 1 to 6, wherein no detectable amount of ethanedithiol is present in the reaction product when analyzing a sample of an effluent of the reactor via gas chromatography to two decimal places for weight percent or to three decimal places for mole percent.

Embodiment 8 is the process of any of embodiments 1 to 7, wherein the reactor is an adiabatic reactor.

Embodiment 9 is the process of any of embodiments 1 to 8, wherein the solid catalyst has weakly basic active groups to allow a conversion of the ethylene oxide by the hydrogen sulfide with a selectivity to beta-mercaptoethanol greater than about 99 wt. % based on a total weight of the ethylene oxide that converts to beta-mercaptoethanol divided by a total weight of the ethylene oxide that converts into the reaction product.

Embodiment 10 is the process of any of embodiments 1 to 9, wherein the solid catalyst comprises a styrene-divinylbenzene copolymer with weakly basic active groups comprising alkyl amines.

Embodiment 11 is the process of any of embodiments 1 to 10, wherein the step of reacting includes a conversion of ethylene oxide to the reaction product which is greater than about 99 wt. % based on a weight of the ethylene oxide that converts to the reaction product divided by a weight of the ethylene oxide fed to the reactor.

Embodiment 12 is the process of any of embodiments 1 to 11, performed at a temperature in a range of about 30° C. to about 80° C.

Embodiment 13 is the process of any of embodiments 1 to 12, wherein the fixed bed of the reactor has a weight average bed temperature of about 65° C. to about 70° C.

Embodiment 14 is the process of any of embodiments 1 to 13, performed at a pressure in a range of about 300 psig to about 500 psig.

Embodiment 15 is the process of any of embodiment 1 to 14, performed at a pressure of about 450 psig.

Embodiment 16 is the process of any of embodiments 1 to 15, wherein a weight hourly space velocity of the ethylene oxide is in a range of about 0.1 to about 1 $hr^{-1}$.

Embodiment 17 is the process of any of embodiments 1 to 16, further comprising recovering a vapor phase of the hydrogen sulfide from the reactor, condensing the vapor phase of the hydrogen sulfide to a liquid phase, and recycling the liquid phase of the hydrogen sulfide to the reactor.

Embodiment 18 is a reactor system for producing beta-mercaptoethanol. The reactor system may be utilized to perform the process of any of embodiments 1 to 17. The reactor system of Embodiment 18 may comprise a reactor; an ethylene oxide stream feeding ethylene oxide to the reactor; a hydrogen sulfide stream feeding hydrogen sulfide to the reactor; a fixed bed containing a solid catalyst placed in the reactor; and an effluent stream flowing from the reactor, wherein the effluent stream comprises a reaction product comprising beta-mercaptoethanol yielded in the reactor by a reaction of hydrogen sulfide and ethylene oxide in presence of the solid catalyst; wherein the solid catalyst comprises a heterogeneous ion exchange resin, and wherein the hydrogen sulfide and the ethylene oxide are present in the reactor during steady state operation in a mole ratio ranging from about 9:1 to about 20:1.

Embodiment 19 is the reactor system of embodiment 18, which includes no internal and/or external source for cooling the reactor.

Embodiment 20 is the reactor system of any of embodiments 18 to 19, wherein the fixed bed of the solid catalyst comprises a top zone, a middle zone, and a bottom zone; and wherein the top zone includes about 66% of a chemically inert solid diluent and about 33% solid catalyst by volume, the middle zone includes about 50% of the chemically inert solid diluent and about 50% solid catalyst by volume, and the bottom zone includes 100% solid catalyst by volume.

Embodiment 21 is the reactor system of any of embodiments 18 to 20, wherein the reaction product of the effluent stream further comprises less than about 0.5 wt. % thiodiglycol.

Embodiment 22 is the reactor system of any of embodiments 18 to 21, wherein the reaction product consists essentially of the beta-mercaptoethanol and the thiodiglycol.

Embodiment 23 is the reactor system of any of embodiments 18 to 22, wherein no detectable amount of ethanedithiol is present in the reaction product when analyzing a sample of the effluent stream via gas chromatography to two decimal places for weight percent or to three decimal places for mole percent.

Embodiment 24 is the reactor system of any of embodiments 18 to 23, wherein a conversion of ethylene oxide to the reaction product in the reactor is greater than about 99 wt. % based on a weight of the ethylene oxide that converts to the reaction product divided by a weight of the ethylene oxide fed to the reactor.

Embodiment 25 is the reactor system of any of embodiments 18 to 24, wherein the solid catalyst has weakly basic active groups to allow a conversion of ethylene oxide by hydrogen sulfide with a selectivity to beta-mercaptoethanol greater than about 99 wt. % based on a total weight of the ethylene oxide that converts to beta-mercaptoethanol divided by a total weight of the ethylene oxide that converts into the reaction product.

Embodiment 26 is the reactor system of any of embodiments 18 to 25, wherein the ethylene oxide stream and the hydrogen sulfide stream each connect directly to the reactor without mixing ethylene oxide and hydrogen sulfide prior to introduction to the reactor.

Embodiment 27 is the reactor system of embodiments 18 to 26, wherein a thermocouple is placed in an end of the ethylene oxide stream which is connected to the reactor, wherein the thermocouple is linked to a controller configured to stop a flow of the ethylene oxide stream upon detecting a temperature in the ethylene oxide stream which is above a threshold temperature.

Embodiment 28 is the reactor system of any of embodiments 18 to 25, wherein the ethylene oxide stream and the hydrogen sulfide stream are each connected to a mixing stream such that ethylene oxide and hydrogen sulfide are mixed prior to introduction to the reactor.

Embodiment 29 is the reactor system of any of embodiments 18 to 25 and 28, wherein a thermocouple is placed in an end of the mixing stream which is connected to the reactor, wherein the thermocouple is linked to a controller configured to stop a flow of the ethylene oxide stream upon detecting a temperature in the mixing stream which is above a threshold temperature.

Embodiment 30 is the reactor system of any of embodiments 18 to 29, wherein the hydrogen sulfide is fed to the reactor in a downflow orientation.

Embodiment 31 is the reactor system of any of embodiments 18 to 30, wherein the reactor is an adiabatic reactor.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the disclosure is not an admission that it is prior art to the present invention, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A reactor system for producing beta-mercaptoethanol, comprising:
   a reactor containing a fixed bed of a solid catalyst comprising a heterogeneous ion exchange resin;
   an ethylene oxide stream comprising ethylene oxide connected directly or indirectly to the reactor;
   a hydrogen sulfide stream comprising liquid hydrogen sulfide connected directly or indirectly to the reactor; and
   an effluent stream connected to the reactor, wherein the effluent stream comprises a reaction product comprising beta-mercaptoethanol and less than about 0.5 wt. % thiodiglycol on a hydrogen sulfide-free basis,
   wherein the fixed bed of the solid catalyst comprises a top zone, a middle zone, and a bottom zone; and wherein the top zone includes about 66% of a chemically inert solid diluent and about 33% solid catalyst by volume, the middle zone in includes about 50% of the chemically inert solid diluent and about 50% solid catalyst by volume, and the bottom zone includes 100% solid catalyst by volume,
   wherein hydrogen sulfide is present in the reactor as a liquid phase and as a gas phase, and
   wherein the reactor is an adiabatic reactor.

2. The reactor system of claim 1, which includes no internal and/or external source for cooling the reactor.

3. The reactor system of claim 1, wherein the reaction product consists essentially of the beta-mercaptoethanol and the thiodiglycol.

4. The reactor system of claim 1, wherein no detectable amount of ethanedithiol is present in the reaction product when analyzing a sample of the effluent stream via gas chromatography to two decimal places for weight percent or to three decimal places for mole percent.

5. The reactor system of claim 1, wherein after a single pass through the reactor a conversion of ethylene oxide to the reaction product in the reactor is greater than about 99 wt. % based on a weight of the ethylene oxide that converts to the reaction product divided by a weight of the ethylene oxide fed to the reactor.

6. The reactor system of claim 1, wherein the solid catalyst has weakly basic active groups to allow a conversion of ethylene oxide by hydrogen sulfide with a selectivity to beta-mercaptoethanol greater than about 99 wt. % based on a total weight of the ethylene oxide that converts to beta-mercaptoethanol divided by a total weight of the ethylene oxide that converts into the reaction product.

7. The reactor system of claim 1, wherein the ethylene oxide stream and the hydrogen sulfide stream each connect directly to the reactor without mixing ethylene oxide and hydrogen sulfide prior to introduction to the reactor.

8. The reactor system of claim 7, wherein a thermocouple is placed in an end of the ethylene oxide stream which is connected to the reactor, wherein the thermocouple is linked to a controller configured to stop a flow of the ethylene oxide stream upon detecting a temperature in the ethylene oxide stream which is above a threshold temperature.

9. The reactor system of claim 1, further comprising a mixing stream that is connected to the ethylene oxide stream, the hydrogen sulfide stream, and the reactor, wherein the mixing stream is configured to mix the ethylene oxide and hydrogen sulfide prior to introduction of the ethylene oxide and hydrogen sulfide to the reactor.

10. The reactor system of claim 9, wherein a thermocouple is placed in an end of the mixing stream which is connected to the reactor, wherein the thermocouple is linked to a controller configured to stop a flow of the ethylene oxide stream upon detecting a temperature in the mixing stream which is above a threshold temperature.

11. The reactor system of claim 1, wherein the hydrogen sulfide stream and the ethylene oxide stream are connected to a top of the reactor.

12. The reactor system of claim 1, wherein the reactor is a plug flow reactor.

13. The reactor system of claim 1, wherein the ethylene oxide stream comprises liquid ethylene oxide.

14. The reactor system of claim 1, wherein after a single pass through the reactor a conversion of ethylene oxide to the reaction product in the reactor is greater than about 99 wt. % based on a weight of the ethylene oxide that converts to the reaction product divided by a weight of the ethylene oxide fed to the reactor.

* * * * *